US006210943B1

(12) United States Patent
Akihama

(10) Patent No.: US 6,210,943 B1
(45) Date of Patent: Apr. 3, 2001

(54) SUCROSE PHOSPHATE SYNTHASE FROM CITRUS AND DNA ENCODING THE SAME

(75) Inventor: Tomoya Akihama, Tama (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 08/853,948

(22) Filed: May 9, 1997

(51) Int. Cl.[7] .............................. C12N 9/10; C07H 21/04
(52) U.S. Cl. ........................................ 435/193; 536/23.2
(58) Field of Search ............................ 435/193; 536/23.2

(56) References Cited

PUBLICATIONS

Lee, C.C. et al., Science, vol. 239, pp. 1288–1291, 1988.*
Ann C. Worrell et al., "Expresseion of a Maize Sucrose Phosphate Synthase in Tomato Alters Leaf Carbohydrate Partitioning," The Plant Cell, vol. 3, pp. 1121–1130, Oct. 1991.
Robert R. Klein et al, "Cloning and Developmental Expression of the Sucrose–Phosphate–Synthase Gene from Spinach," Planta, vol. 190, No. 4, pp. 498–510, 1993.
Holger Hesse et al., "Cloning and Expression Analysis of Sucrose–Phosphate Synthase from Sugar Beet (Beta Vulgaris L.)," Mol Gen Genet, vol. 247, pp. 515–520, 1995.
A. Komatsu et al., Programme and Abstracts, VIII Congress of the International Society of Citriculture, May 1996, P039, p. 97.
Akira Komatsu et al., "Cloning and Molecular Analysis of cDNAs Encoding Three Sucrose Phosphate Synthase Isoforms from a Citrus Fruit (Citrus Unshiu Marc.)," Mol Gen Genet, vol. 252, pp. 346–351, 1996.
Akira Komatsu, "Molecular and Physiological Characterization for Sucrose–Metabolizing Enzymes and Genes in Sink Tissues of Citrus," pp. 1–97, 1996. Thesis, Meiji University.

* cited by examiner

Primary Examiner—Ponnathapu Achutamurthy
Assistant Examiner—Peter P. Tung
(74) Attorney, Agent, or Firm—Oblon, Spivak, McClelland, Maier & Neustadt, P.C.

(57) ABSTRACT

This invention relates to DNA encoding a sucrose phosphate synthase from Citrus having an amino acid sequence shown in SEQ ID NO:2, or an isoform thereof sharing at least 50% homology with the sucrose phosphate synthase in amino acid level. It also relates to a sucrose phosphate synthase from Citrus having an amino acid sequence shown in SEQ ID NO:2, or an isoform as defined above.

4 Claims, 14 Drawing Sheets

```
pSPS1(CitSPS1): QVKYVVELARALGSMPGVYRVDLLTRQVSAPDVDWSYGEPTEML---TPRNSDDFMDDMG
pSPS2          :............ANTE..........IAS.E..S.....N...---S--CPS.--G-T.
pSPS3          :.I.........AR.........FS....S.E........A...---.GGPE..GI-EV.
SoSPS          :...................G............SSRNSE..TE---QL.           60
                * ********    ***     *  * * pSPS1(CitSPS1): ESSGAYIIRIPFGPKDKYIAKELLWPHIPEFVDGALNHIIRMSNVLGEQIGGGKPVWPVA
pSPS2          :-.C........C.AR......S...Y.H.........VN.ARAI...VN....T.XYV
pSPS3          :............R...LR......Y.Q......A.CLN..K.........Q....YV
SoSPS          :..................V.......Y......S..KQ..K.........L....AS 120
                * ******** * *  *** * ******* *   *    *  * * pSPS1(CitSPS1): IHGHYADAGDSAALLSGALNVPMLFTGHSLGRDKLEQLLKQARLSRDEINATYKIMRRIE
pSPS2          :........EV.GH.P.G.....VL.......N.F......G..P-KD...S......F.
pSPS3          :......................VL.......N........G.Q.KED..S.........
SoSPS          :V....................V..........D.....G...E.VD..........   180
                ********  *  *  * *** *****  *  ***** *         ****** * pSPS1(CitSPS1): AEELSLDASEIVITSTRQEIEEQWRLYDGFDPVLERKLRARIKRNVSCYGKFMPRMAIIP
pSPS2          :....G.....M.V.......M..G......LK......V.RQ.G...F.R.....VV..
pSPS3          :G.......A.L.....K...D...G.......VK..KV....AR.GGN.HDRY....VV..
SoSPS          :....C................Q..H...L........MR.G...H.R......K..   240
                * * * * * *   *    ** *  *      ** pSPS1(CitSPS1): PGMEFHHIVPQ-DG-DMDGE-T---EGNEDNPASPDPPIWSEIMRFFTNPRKPVILALAR
pSPS2          :...D.-SY.TTQ.TMGG.TDLKSLIVNDRTQTTRNL..M...V.......H..T....S.
pSPS3          :...D.SNV.A.E.TPEV...L.SLIG.TDGSSPKAI.A...DV...L...H..M....S.
SoSPS          :......-NHIAPE.---A.--MDTDID.HKESN.N...V.........S.G...M......  300
                *** *     *   *                   *  * *   ** * pSPS1(CitSPS1): PDPKKNITTLVKAFGECRPLRELANLTLINGNRDGIDEMSSTSASVLLSVLK
pSPS2          :......V...L......Q......M..L....D.ED..NS.SV..TT..N
pSPS3          :........L.........F......M...D.E...GN....IT...
SoSPS          :......L.....................I....D.....T..S...I.I..        352
                ****** *** ****** **** ** *** **** * **     **  *
```

FIG. 2

```
CAACAAGAAGAAGAAGAAGAAGATGGCAGGAAACGATTGGATAAACAGTTACCTCGAAGCAATACTTGATGTGGGCCCGGTCTCGA    90
                      M  A  G  N  D  W  I  N  S  Y  L  E  A  I  L  D  V  G  P  G  L  D

CGACGCTAAATCCTCGCTGCTCTTGCGAGAGAGGGAGGTTCAGTCCGACGAGGTACTTCGTGGAGGAAGTCATCACCGGATTCGATGA   180
 D  A  K  S  S  L  L  R  E  R  G  R  F  S  P  I  R  Y  F  V  E  E  V  I  T  G  F  D  E

GACCGATCTCCACCGTTCCTGGGTTAAGGCTCAAGGACGAGGAGTCTCAAGAGGAATACGCGGCTGGAGAACATGTGTTGGAGGAT   270
 T  D  L  H  R  S  W  V  K  A  Q  A  T  R  S  P  Q  E  R  N  T  R  L  E  N  M  C  W  R  I

TTGGAACTTGGCTCTGTCAGAAAAAGCAGCTTGAGGGAGAGGCAGCTCAGAGAATGGCGAAACGTCTCTTGAACGTGAAAGAGGCCGGAG   360
 L  E  L  G  S  V  R  K  S  S  L  E  G  E  A  A  Q  R  M  A  K  R  R  L  E  R  E  R  R

GGAAGCAACTGCTGATATGTCTGAAGACTTGTCTGAGGGAGAAAAAGGGACATTGTCAGGATGTATCGGCTCATGGTGATAGTACTAG   450
 E  A  T  A  D  M  S  E  D  L  S  E  G  E  K  G  D  I  V  S  D  V  S  A  H  G  D  S  T  R

AAGCAGACTACCTAGAATAAGCTCTGTTGATGCAATGGAAACATTGGATTAGTCAACAGAAGGAAAAAAGCTATATATGTGTTAATAAG   540
 S  R  L  P  R  I  S  S  V  D  A  M  E  T  W  I  S  Q  Q  K  G  K  K  L  Y  I  V  L  I  S

CATTCATGGTCTCATCGAGGTGAAAATATGGAGTTGGGCCGTGATTCTGATACTGGTGGTCAGGTTAAGTATGTTGTGGAACTTGCAAG   630
 I  H  G  L  I  R  G  E  N  M  E  L  G  R  D  S  D  T  G  G  Q  V  K  Y  V  V  E  L  A  R

AGCCTTGGGCTCCATGCCAGGAGTTTATCGAGTTGATTGCTCACTAGACAAGTATCGGCACCGGATGTAGATTGGAGTTATGGTGAACC   720
 A  L  G  S  M  P  G  V  Y  Y  R  V  D  L  L  T  R  Q  V  S  A  P  D  V  D  W  S  Y  G  E  P
```

*FIG. 3A*

```
CACAGAGATGCTGACTCCACGCAACTCAGATGATTCATGGACGATATGGGGAGAGCAGCGGTGCTTATATCATTCGAATACCATTGG   810
 T  E  M  L  T  P  R  N  S  D  D  F  M  D  D  M  G  E  S  S  G  A  Y  I  I  R  I  P  F  G

ACCAAAAGATAAATATCGCTAAAGAACTTTATGGCCTCACATCCCTGAGTTGTTGATGGTGCACTCAACCATATCATACGGATGTC   900
 P  K  D  K  Y  I  A  K  E  L  L  W  P  H  I  P  E  F  V  D  G  A  L  N  H  I  I  R  M  S

CAATGTTCTAGGGGAGCAAATTGGTGGTGGGAAGCCAGTCTGCCTGTTGCCATCCATGGGCATTATGCAGATGCAGGTGACTCAGCTGC   990
 N  V  L  G  E  Q  I  G  G  G  K  P  V  W  P  V  A  I  H  G  H  Y  A  D  A  G  D  S  A  A

CCTTCTATCCGGTGCTCTTAACGTGCCAATGCTTTTTACTGGCCATTCACTTGGCCGTGATAAGTTAGAGCAGCTTTTAAAACAAGCTCG   1080
 L  L  S  G  A  L  N  V  P  M  L  F  T  G  H  S  L  G  R  D  K  L  E  Q  L  L  K  Q  A  R

ATTATCGAGGGATGAAATAAATGCTACGTACAAATAATGCGTCGAATAGAGGCTGAGGAATTATCCCTTGATGCCTCTGAAATAGTGAT   1170
 L  S  R  D  E  I  N  A  T  Y  K  I  M  R  R  I  E  A  E  E  L  S  L  D  A  S  E  I  V  I

AACTAGCACTAGGCAGGAGAGATAGAAGAGCAATGGCGTTTATATGATGGTTTGATCCTGTACTAGAGCGTAAACTACGAGCCAGGATTAA   1260
 T  S  T  R  Q  E  I  E  E  Q  W  R  L  Y  D  G  F  D  P  V  L  E  R  K  L  R  A  R  I  K

ACGTAATGTGAGCTGTTATGGCAAGTTCATGCCTCGCATGGCTATAATTCCTCCTGAATGGAGTTCCATCATATTGTTCCCAAGATGG   1350
 R  N  V  S  C  Y  G  K  F  M  P  R  M  A  I  I  P  P  G  M  E  F  H  H  I  V  P  Q  D  G

TGATATGGATGGTGAAACAGAAGGAAATGAAGACAATCCTGCTTCTCCAGATCGGCTATCTGGTCTGAGATAATGCCTTCTTTACAAA   1440
 D  M  D  G  E  T  E  G  N  E  D  N  P  A  S  P  D  P  P  I  W  S  E  I  M  R  F  F  T  N
```

*FIG. 3B*

```
CCCACGTAAGCCTGTGATTCTTGCACTTGCTAGGCCGGATCCAAAAAAGAATATCACAACTTTGGTTAAAGCATTTGGAGAATGTCGTCC    1530
 P R K P V I L A L A R P D P K K N I T T L V K A F G E C R P

ATTAAGAGAGCTTGCTAATCTTACTCTGATTAATGGTAACCGAGATGGGATTGATGAAATGTCAAGCACAAGTGCTTCTGTTCTTCTCTC    1620
 L R E L A N L T L I N G N R D G I D E M S S T S A S V L L S

AGTGCTGAAGCTTACTGACAAATATGATCTGTATGGGCAAGTTGCATACCCGAAACATCATAAACAATCTGATGTCCTGAAATATATCG    1710
 V L K L T D K Y D L Y G Q V A Y P K H H K Q S D V P E I Y R
```

*FIG. 3C*

```
TCTGGCAGCAAAGACAAAGGGTGTTTCATAAATCCAGCTTTTATAGAGCCTTTTGGGCTTACTTGATTGAGGCAGCGGCTCATGGTTT  1800
 L  A  A  K  T  K  G  V  F  I  N  P  A  F  I  E  P  F  G  L  T  L  I  E  A  A  A  H  G  L

GCCCATTGTGGCCACTAAGAATGGAGGACCTGTTGATATACATCGGGTTCTTGACAATGGTCTTCTTGTCGATCCCCATGATCAGCAGTC  1890
 P  I  V  A  T  K  N  G  G  P  V  D  I  R  R  V  L  D  N  G  L  L  V  D  P  H  D  Q  Q  S

TATTGCTGATGCTCTCTTAAGCTTGTTGCTGGTAAGCAACTTGGGCAAGGTGTCGACAGAATGGATTGAAGAACATTCACCTATTTC  1980
 I  A  D  A  L  L  K  L  V  A  G  K  Q  L  W  A  R  C  R  Q  N  G  L  K  N  I  H  L  F  S

TTGGCCAGAGCACTGTAAAACTTACCTATCTCGTATAGCCGGTTGCAAACCCAGGCATCCGCAGTGGCAGAGAACTGATGATGGAGGTGA  2070
 W  P  E  H  C  K  T  Y  L  S  R  I  A  G  C  K  P  R  H  P  Q  W  R  T  D  D  G  G  E

GACATCAGAGTCAGATTCACCAGGTGATTCCTTGAGAGATATACAGGATATATCTTGAACTTGAAGTTTCATTGGATGGAGAAAGAG  2160
 T  S  E  S  D  S  P  G  D  S  L  R  D  I  Q  D  I  S  L  N  L  K  F  S  L  D  G  E  K  S

TGGAGCTAGTGGAAATGATGATTCTTTAGACTCTGAAGGAAATGTTGCCGACAGAAAGAGTAGGTTGGAGAATGCTGTTCTGGCATGGTC  2250
 G  A  S  G  N  D  D  S  L  D  S  E  G  N  V  A  D  R  K  S  R  L  E  N  A  V  L  A  W  S

AAAGGGTGTTCTGAAAGATACCCGAAAGTCTGGTTCCACAGATAAAGTGGACCAGAATACAGGTGCTGCTAAGTTCCAGCATTGAGGAG  2340
 K  G  V  L  K  D  T  R  K  S  G  S  T  D  K  V  D  Q  N  T  G  A  A  K  F  P  A  L  R  R

GCGGAAGCATATCTTTGTCATTTCTGTGGATTGTGATAGCACTACAGGTCTTCTTGATGCGACTAAGAAGATCTGTGAGGCTGTGGAAAA  2430
 R  K  H  I  F  V  I  S  V  D  C  D  S  T  T  G  L  L  D  A  T  K  K  I  C  E  A  V  E  K
```

*FIG. 3D*

```
GGAAAGGACTGAAGGCTCTATAGGGTCATATTGTCAACATCAATGACCATATCTGAGATTCACTCTTTTCTGTATCAGGTCACTTGAG   2520
 E  R  T  E  G  S  I  G  F  I  L  S  T  S  M  T  I  S  E  I  H  S  F  L  V  S  G  H  L  S

CCCTAGTGATTTTGATGCCTTATTTGTAACAGTGGCAGTGATCTCTACTATTCAACTCTTAATTCTGAGGATGGCCCTTCGTGGTTGA   2610
 P  S  D  F  D  A  F  I  C  N  S  G  S  D  L  Y  Y  S  T  L  N  S  E  D  G  P  F  V  V  D

CTTCTATTACCACTCACACATTGAATATCGTTGGGTGGGAAGGACTGAGGAAGACTTTGGTCCGGTGGGCATCTCAAGTTACTGATAA   2700
 F  Y  Y  H  S  H  I  E  Y  R  W  G  G  E  G  L  R  K  T  L  V  R  W  A  S  Q  V  T  D  K

AAAGGCGGAGAGTGGAGAAAAGGTTTTGACACCAGCTGAACAACTTTCAACCAACTACTGCTATGCTTTAGTGTGCAAAAGCTGGAAT   2790
 K  A  E  S  G  E  K  V  L  T  P  A  E  Q  L  S  T  N  Y  C  Y  A  F  S  V  Q  K  P  G  M

GACTCCCCTGTTAAGGAGCTTCGAAGGTGCTGAGAATTCAAGCGCTTCGTTGTCATGTTATTTATTGCAAAATGTAGCAGGGTTAA    2880
 T  P  P  V  K  E  L  R  K  V  L  R  I  Q  A  L  R  C  H  V  I  Y  C  Q  N  G  S  R  V  N

TGTAATTCCAGTTTTTGGCATCACGTTCCCAGGCTCTGAGGTATCTATATCTTCGGTGGGTGTGGAGTTGTCAAAGATGGTGGTTTTGT  2970
 V  I  P  V  L  A  S  R  S  Q  A  L  R  Y  L  Y  L  R  W  G  V  E  L  S  K  M  V  V  F  V

TGGGGAGTCTGGGGACACGGACTACGAAGGATTGCTTGGGGTGCACAAAACTGTAATATTGAAGGGCATTGCAGTAGTTCAAGCAA    3060
 G  E  S  G  D  T  D  Y  E  G  L  L  G  G  V  H  K  T  V  I  L  K  G  I  C  S  S  S  S  N

TCAAATCCATGCTAACCGAAGCTACCCTCTCTCAGATGTCATGCCAACATTGACAGTCCCAACATTGTTCAGAGCGCTGAAGATTGCACAAC  3150
 Q  I  H  A  N  R  S  Y  P  L  S  D  V  M  P  I  D  S  P  N  I  V  Q  T  P  E  D  C  T  T
```

*FIG. 3E*

```
TTCTGATATCCGCAGTTCTTGGAGCAATTAGGACTTCTTAAGGTCTGAAAGGTTTCAGCCTTGTCTCCGCTCCCTCCTTATCCTTTCGTT    3240
 S  D  I  R  S  S  L  E  Q  L  G  L  L  K  V  *

TAAATTCATCTGAGATCTTCTCATGTCTGACATTGTTCATATTTGGGTCTTTCTCTGTTGGCCTTGTTATGCAAAGCATTCTCTC       3330
AGTTTTTATCTCTTCTTCCATTTGTATATTCACTGAAACCCAAAGACTGATGTCTTGTGCTATCGGCCTTATTTGTCAA              3420
TGAGCCAGATCACTTGCAGATGAAATCTGGATGAAAATAATTACGAGTTACTTGGTATAAATTGTAAAATAAACGCCTTTTGTCCGCATG   3510
AGACTATTACACAAATGAAAGCAGTGTTG                                                                3539
```

*FIG. 3F*

```
ZmSPS   : MAGNEWINGYLEAILDSHTSSRGAGGGGGGDPRSPTKAASPRGAHMNFNPSHYFVEEVVKGVDESDLHRTWIKVVATRN
SoSPS   : .....D...S.........--VGGQ.IDAST,KTSTAP,SLLRE.,---H.S..R......IS.F..T....S.VRAAS..S
BvSPS1  : .....D...S.........--V-GP.LD--DAK-S----SLLRE.,---R.S.TR......IT.F..T....S.VRAQ...S
CitSPS1 : .....D...S.........--V-GP.LD--DAK-S----SLLRE.,---R.S.TR......IT.F..T....S.V.AQ...S
          ****.***.********                  *       **  * ****** ** **** *         80

ZmSPS   : ARERSTRLENMCWRTWHLARKKKQLELEGIQRISARRKEQEQVRREATEDLAEDLSEGEKGDTIGE-LAPVETTKKKFQR
SoSPS   : PQ.N......L......N.......I.G.EA..LAK.HV.R.RG.....A.MS.......R...VADM.FAS.S..GRMR.
BvSPS1  : PQ.N...........N........N.EA..KTK..M.L.RG......A.MS...........-,HGDS.RPRLP,
CitSPS1 : PQ.N...........N........G.AA..MAK..L.R.RG......A.MS..........IVSDVS.HGDS.RSRLP.
          ** *   ***  *** ** ** ** * *****  * **  *****               * *          160

ZmSPS   : NFSDLTVWSDDN--KEKKLYIVLISYHGLVRGENMELGRDSDTGGQVKYVVELARAMSMPGVYRVDLFTRQVSSPDVDW
SoSPS   : ISSVEMMDN.ANTF......V....L....I..............................LGS.........A.G...
BvSPS1  : INSLDAMET.ISQQ...........L....L..............................LGS.........L....
CitSPS1 : ISSVDAMET.ISQQ.G..............I..I............................LGS.........A....
          **  **** ****  *                                       **** ***** * *** 240

ZmSPS   : SYGEPTEMLCA-GS------NDGEGMGESGGAYIVRIPCGPRDKYLKKEALWPYLQEFVDGALAHILNMSKALGEQVGNGRP
SoSPS   : ..........SSRN.--E.ST.QL...S.....I..F.K...VA.L...IP.......S..KQ..V....I.G.L.
BvSPS1  : ..........NPRD.NGFDD.DDE......S.........F.......IA.E....IP......N.VQ..V....I.S.ET
CitSPS1 : ..........TPRN.DDF--MDD-......S.....I..F.K..IA.L..HIP......N.IR..NV....I.G.K.
          **********      ***  ****  **  ** **  * ** ***** * *** * *** *  **  ** * **   320
```

FIG. 4A

```
ZmSPS    : VLPYVIHGHYADAGIDVAALLSGALNVPMVLTGHSLGRNKLEQLLKQGRMSKEEIDSTYKIMRRIEGEELALDASELVITS
SoSPS    : .W.ASV.............S.......F.........D.D.....L.R..V.A.........A...C.....I.....
BvSPS1   : .M.VA..............S......G..L.......D..........DD.NN..........A...S.....I.....
CitSPS1  : .W.VA..............S........LF......D........A.L.RD..NA.......A...S.....I.....
           * * ************ ****** ****       ** ******* **** ***** ***** ****      400

ZmSPS    : TRQEIDEQWGLYDGFDVKLEKVLRARARRGVSCHGRYMPRMVVIPPGMDFSNVVVHEDIDGDGDVKDDIVGLEGASPKSM
SoSPS    : .......E...Q..H...LV..RK.....M.......F.....AK......E.NH-IAP-E.A.M.TDI.GHKESN.N.-D-
BvSPS1   : .......E..H.......PV..RK.....MK.....Y..F...........E.NH-I.P-HE..M.GETEETEEHPT..-D-
CitSPS1  : .......E..R.......PV..RK.....IK.N...Y.KF...AI......E.HH-I.P-Q...M.GETEGNEDNP...-D-
           ***** *** **** ** **** **        ** *** * **** *     **  *  *                480

ZmSPS    : PPIWAEVMRFLTNPHKPMILALSRPDPKKNITTLVKAFGECRPLRELANLTLIMGNRDDIDDMSAGNASVLTTVLKLIDK
SoSPS    : .V..S.I...FS.GR.........A..........L....................I......E..TISS......ISI......
BvSPS1   : ......I...FSK.R.........A...............................G.E..STSS....LS......Q
CitSPS1  : ..S.I..F...R..V..A..........................................N...G.E..STS....LS....T...
           * ** *** ****** ** ****** ****************** *****  **** ** *** *** * 560

ZmSPS    : YDLYGSVAFPKHHNQADVPEIYRLAAKMKGVFINPALVEPFGLTLIEAAAHGLPIVATKNGGPVDITNALNNGLLVDPHD
SoSPS    : .......Q..Y....K.S...D.......T........FI........Y................IGV.D....I......
BvSPS1   : .......Q..Y....K..............T........FI.....................M.......QRV.D.....E
CitSPS1  : .......Q..Y....K.S.............T........FI..............................HRV.D.........
           ***** ** *** **** ******   ************* *** *************        * **** *** 640
```

*FIG. 4B*

```
ZmSPS   : QNAIADALLKLVADKNLWQECRRNGLRNIHLYSWPEHCRTYLTRVAGCRLRNPRWLKDTPADAGADEEFLEDSM-DAQD
SoSPS   : .KS.............H..TK..Q....K.....F.........KN..S.I.S.KP.Q.N.QR-IDEGSENSDTDSAG..LR..I..
BvSPS1  : ..QS..T..........Q..TK.QQ....K.........SK....S.I.SS.Q.Q.Q.QRSSDEGLDNQ.P.SPS..LR.IK.
CitSPS1 : ..QS............G.Q..AR..Q....K.....F......K...S.I...KP.H.Q.QRTDDGG-ETS.SDSPG..LR.I..
            * ** ******** * ** * *** **** *****          ** * ***                               720

ZmSPS   : LSLRL--SIDGEKSSLNTNDPLWFDPQDQVQKIMNNIKQSSALPPSMSSVAAEGTGSTMNKYPLLRRRRRLF-VIAVDCY
SoSPS   : I..N.KL.L.A.---RTEGGNSF--DDSLDSEEA..A.RKIE-N-AVAK-LSK--SMDKAQVDVGNLKFPAIRRRKCIFV
BvSPS1  : I..N.E-VL-V-RPEKRVK--TLKILGLMTKANSRM--LLCSWSNGVHKMLRKARF.DKVDQ--ASSKYPA.RRRKLIYV
CitSPS1 : I..N.KF.L....GASG..DSLDSEGNVADRKSRLENAVL.WSKGVLKDTRKSGSTDKVDQNTGAAKFPALRRRKHIFV
            ** *                                                                             800

ZmSPS   : QDDGRASKKMLQVIQEVFRAVRSDSQMFKISGFTLSTAMPLSETLQLLQLGKIPATDFDALICGSGSEVYYPGTANCMDA
SoSPS   : IALDCDVTSD.LQVIKTVISIVGEQRPTGSI..I...S.T..VDS..DS.GLRPA....F..N....L..---PSTDYS
BvSPS1  : IAVDGDYEDG.FD.VRRIFDAAGKEKIEGSI..I...SYSMP.IQNY.LSKGFNLH...Y..N...L..---SSLNSE
CitSPS1 : ISVDCD.TTG.LDATKKICEAVEKERTEGSI..I...S.TI..IHSF.VS.HLSPS....F..N...DL..---STLNSE
             *  ***       *           * *                **** ** ***  *  **                  880

ZmSPS   : EGKLRPDQDYLMHISHRWSHDGARQTI---AKLMGAQ--DGSGDAVEQDVASSNAHCVAFLIKDPQKVKTVDEMRERLRM
SoSPS   : ..SPFVL...YS..DY..GGE.LWK.LVKW.ASVNEKKGENAPNI.IA.ET..TT..Y..KVN.FILAPPAK.L.KMM.I
BvSPS1  : ..SNIIA.S..HS..EY..GGE.L.R.LLRW.ASITEKNGENEEQVITE.EEV.TGY.F..K..NQN..PPTK.L.KSM.I
CitSPS1 : D.PFVV.FY.HS..EY..GGE.L.K.LVRW.SQVTDKKAESGEKVLTPAEQL.TNY.Y..SVQK.GMTPP.K.L.KV..I
            *  *  *  ** * *  ** * ***  * *   ** ***                                          960
```

FIG. 4C

```
ZmSPS   : RGLRCHIMYCRNSTRLQVVPLLASRSQALRYLSVRWGVSVGNMYLITGEHGDTDLEEMLSGLHKTVIVRGVTEKGSEALV
SoSPS   : QA....AI..Q.G...N.I.V...........FM....ELS.FVVFV..S....Y.GL.G.V.....LK.--IGSNTSNF
BvSPS1  : QA....VI..Q.GSKMN.I.V...............Y.....ELSK.VVEV..C....Y.GL.G.V.....LK.-VSNTALRSL
CitSPS1 : QA....VI..Q.GS.VN.I.V...............YL....ELSK.VVFV..S....Y.GL.G.V.....LK.-ICSS.SNQI   1040
           ****  **  * * ***********  ****    ** ****  ****    * * *****  *

ZmSPS   : RSPGSYKRDDVVPSETPLAAYTTGELKADEI-MRALKQVS-KTSSGM
SoSPS   : HATRA.PMEH.M.VDS..NM-FQ..GCNI..D.SDALS.IGCL.AQKSL
BvSPS1  : HANR..PLSH..SLDS.NIGEVSKGCSSS..QSIVT.LS--.A----
CitSPS1 : HANR..PLS...M.IDS.NIVQ.PEDCTTSD.RSSLEQLGLL.V----   1087
            *      *                                 *
```

*FIG. 4D*

SEQUENCE LISTING

<160> NUMBER OF SEQ ID NOS: 10

<210> SEQ ID NO 1
<211> LENGTH: 3539
<212> TYPE: DNA
<213> ORGANISM: Citrus unshiu

<400> SEQUENCE: 1

| | | | | | |
|---|---|---|---|---|---|
| caacaagaag | aagaagaaga | agaagatggc | aggaaacgat | tggataaaca | gttacctcga | 60 |
| agcaatactt | gatgtgggcc | ccggtctcga | cgacgctaaa | tcctcgctgc | tcttgcgaga | 120 |
| gagagggagg | ttcagtccga | cgaggtactt | cgtcgaggaa | gtcatcaccg | gattcgatga | 180 |
| gaccgatctc | caccgttcct | gggttaaggc | tcaagcgacg | aggagtcctc | aagagaggaa | 240 |
| tacgcggctg | gagaacatgt | gttggaggat | ttggaacttg | gctcgtcaga | aaaagcagct | 300 |
| tgagggagag | gcagctcaga | gaatggcgaa | acgtcgtctt | gaacgtgaaa | gaggccggag | 360 |
| ggaagcaact | gctgatatgt | ctgaagactt | gtctgaggga | gaaaaagggg | acattgtcag | 420 |
| cgatgtatcg | gctcatggtg | atagtactag | aagcagacta | cctagaataa | gctctgttga | 480 |
| tgcaatggaa | acatggatta | gtcaacagaa | aggaaaaaag | ctatatattg | tgttaataag | 540 |
| cattcatggt | ctcatacgag | gtgaaaatat | ggagttgggc | cgtgattctg | atactggtgg | 600 |
| tcaggttaag | tatgttgtgg | aacttgcaag | agccttgggc | tccatgccag | gagtttatcg | 660 |
| agttgatttg | ctcactagac | aagtatcggc | accggatgta | gattggagtt | atggtgaacc | 720 |
| cacagagatg | ctgactccac | gcaactcaga | tgatttcatg | gacgatatgg | gggagagcag | 780 |
| cggtgcttat | atcattcgaa | taccatttgg | accaaaaagat | aaatatatcg | ctaaagaact | 840 |
| tttatggcct | cacatccctg | agtttgttga | tggtgcactc | aaccatatca | tacggatgtc | 900 |
| caatgttcta | ggggagcaaa | ttggtggtgg | gaagccagtc | tggcctgttg | ccatccatgg | 960 |
| gcattatgca | gatgcaggtg | actcagctgc | ccttctatcc | ggtgctctta | acgtgccaat | 1020 |
| gcttttttact | ggccattcac | ttggccgtga | taagttagag | cagcttttaa | aacaagctcg | 1080 |
| attatcgagg | gatgaaataa | atgctacgta | caaaataatg | cgtcgaatag | aggctgagga | 1140 |
| attatcccctt | gatgcctctg | aaatagtgat | aactagcact | aggcaggaga | tagaagagca | 1200 |
| atggcgttta | tatgatggtt | ttgatcctgt | actagagcgt | aaactacgag | ccaggattaa | 1260 |
| acgtaatgtg | agctgttatg | gcaagttcat | gcctcgcatg | gctataattc | ctcctggaat | 1320 |
| ggagttccat | catattgttc | cccaagatgg | tgatatggat | ggtgaaacag | aaggaaatga | 1380 |
| agacaatcct | gcttctccag | atccgcctat | ctggtctgag | ataatgcgct | tctttacaaa | 1440 |
| cccacgtaag | cctgtgattc | ttgcacttgc | taggccggat | ccaaaaaaga | atatcacaac | 1500 |
| tttggttaaa | gcatttggag | aatgtcgtcc | attaagagag | cttgctaatc | ttactctgat | 1560 |
| taatggtaac | cgagatggga | ttgatgaaat | gtcaagcaca | agtgcttctg | ttcttctctc | 1620 |
| agtgctgaag | cttactgaca | aatatgatct | gtatgggcaa | gttgcatacc | cgaaacatca | 1680 |
| taaacaatct | gatgttcctg | aaatatatcg | tctggcagca | aagacaaagg | gtgttttcat | 1740 |
| aaatccagct | tttatagagc | cttttgggct | tactttgatt | gaggcagcgg | ctcatggttt | 1800 |

-continued

```
gcccattgtg gccactaaga atggaggacc tgttgatata catcgggttc ttgacaatgg      1860
tcttcttgtc gatccccatg atcagcagtc tattgctgat gctcttctta agcttgttgc      1920
tggtaagcaa ctttgggcaa ggtgtcgaca gaatggattg aagaacattc acctattttc      1980
ttggccagag cactgtaaaa cttacctatc tcgtatagcc ggttgcaaac ccaggcatcc      2040
gcagtggcag agaactgatg atggaggtga gacatcagag tcagattcac caggtgattc      2100
cttgagagat atacaggata tatctttgaa cttgaagttt tcattggatg agaaaagag       2160 tggagctagt ggaaatgatg attctttaga ctctgaagga aatgttgccg acagaaagag      2220
taggttggag aatgctgttc tggcatggtc aaagggtgtt ctgaaagata cccgaaagtc      2280
tggttccaca gataaagtgg accagaatac aggtgctgct aagtttccag cattgaggag      2340
gcggaagcat atctttgtca tttctgtgga ttgtgatagc actacaggtc ttcttgatgc      2400
gactaagaag atctgtgagg ctgtggaaaa ggaaaggact gaaggctcta tagggttcat      2460
attgtcaaca tcaatgacca tatctgagat tcactctttt ctggtatcag gtcacttgag      2520
ccctagtgat tttgatgcct ttatttgtaa cagtggcagt gatctctact attcaactct      2580
taattctgag gatggcccct tcgtggttga cttctattac cactcacaca ttgaatatcg      2640
ttggggtggg gaaggactga ggaagacttt ggtccggtgg gcatctcaag ttactgataa      2700
aaaggcggag agtggagaaa aggttttgac accagctgaa caacttttcaa ccaactactg      2760 ctatgctttt agtgtgcaaa agcctggaat gactcccccct gttaaggagc ttcggaaggt      2820
gctgagaatt caagcgcttc gttgtcatgt tatttattgc caaaatggta gcaggttaa       2880 tgtaattcca gttttggcat cacgttccca ggctctgagg tatctatatc ttcggtgggg      2940
tgtggagttg tcaaagatgg tggtttttgt tggggagtct ggggacacgg actacgaagg      3000
attgcttggg ggtgtgcaca aaactgtaat attgaagggc atttgcagta gttcaagcaa      3060
tcaaatccat gctaaccgaa gctaccctct ctcagatgtc atgccaattg acagtcccaa      3120
cattgttcag acgcctgaag attgcacaac ttctgatatc cgcagttctt tggagcaatt      3180
aggacttctt aaggtctgaa aggtttcagc cttgtctcgc tccctcctta tcctttcgtt      3240
taaattcatc tgagatcttc tcatgtctgt ctgacattgt tcatatttgg gtctttctct      3300
gttggccttg ttatgcaaag cattctcttc agtttttttat ctctttcttc cattttgtat      3360
attcactgaa accccaaaag actcgatgtc ttgttgctgc tatcggcctt attttgtcaa      3420
tgagccagat cacttgcaga tgaaatctgg atgaaaataa ttcgagttta cttggtataa      3480
attgtaaaat aaacgccttt tgtccgcatg agactattac acaaatgaaa gcagtgttg       3539
```

<210> SEQ ID NO 2
<211> LENGTH: 1057
<212> TYPE: PRT
<213> ORGANISM: Citrus unshiu

<400> SEQUENCE: 2

Met Ala Gly Asn Asp Trp Ile Asn Ser Tyr Leu Glu Ala Ile Leu Asp
 1               5                  10                  15

Val Gly Pro Gly Leu Asp Asp Ala Lys Ser Ser Leu Leu Leu Arg Glu
            20                  25                  30

Arg Gly Arg Phe Ser Pro Thr Arg Tyr Phe Val Glu Val Ile Thr
        35                  40                  45

Gly Phe Asp Glu Thr Asp Leu His Arg Ser Trp Val Lys Ala Gln Ala
    50                  55                  60

Thr Arg Ser Pro Gln Glu Arg Asn Thr Arg Leu Glu Asn Met Cys Trp

```
            65                  70                  75                  80
Arg Ile Trp Asn Leu Ala Arg Gln Lys Lys Gln Leu Glu Gly Glu Ala
                85                  90                  95
Ala Gln Arg Met Ala Lys Arg Arg Leu Glu Arg Glu Arg Gly Arg Arg
               100                 105                 110
Glu Ala Thr Ala Asp Met Ser Glu Asp Leu Ser Glu Gly Glu Lys Gly
               115                 120                 125
Asp Ile Val Ser Asp Val Ser Ala His Gly Asp Ser Thr Arg Ser Arg
               130                 135                 140
Leu Pro Arg Ile Ser Ser Val Asp Ala Met Glu Thr Trp Ile Ser Gln
145                149150                 155                 160
Gln Lys Gly Lys Lys Leu Tyr Ile Val Leu Ile Ser Ile His Gly Leu
               165                 170                 175
Ile Arg Gly Glu Asn Met Glu Leu Gly Arg Asp Ser Asp Thr Gly Gly
               180                 185                 190
Gln Val Lys Tyr Val Val Glu Leu Ala Arg Ala Leu Gly Ser Met Pro
               195                 200                 205
Gly Val Tyr Arg Val Asp Leu Leu Thr Arg Gln Val Ser Ala Pro Asp
    210                 215                 220
Val Asp Trp Ser Tyr Gly Glu Pro Thr Glu Met Leu Thr Pro Arg Asn
225                 230                 235                 240
Ser Asp Asp Phe Met Asp Asp Met Gly Glu Ser Ser Gly Ala Tyr Ile
                245                 250                 255
Ile Arg Ile Pro Phe Gly Pro Lys Asp Lys Tyr Ile Ala Lys Glu Leu
                260                 265                 270
Leu Trp Pro His Ile Pro Glu Phe Val Asp Gly Ala Leu Asn His Ile
            275                 280                 285
Ile Arg Met Ser Asn Val Leu Gly Glu Gln Ile Gly Gly Gly Lys Pro
    290                 295                 300
Val Trp Pro Val Ala Ile His Gly His Tyr Ala Asp Ala Gly Asp Ser
305                 310                 315                 320
Ala Ala Leu Leu Ser Gly Ala Leu Asn Val Pro Met Leu Phe Thr Gly
                325                 330                 335
His Ser Leu Gly Arg Asp Lys Leu Glu Gln Leu Leu Lys Gln Ala Arg
            340                 345                 350
Leu Ser Arg Asp Glu Ile Asn Ala Thr Tyr Lys Ile Met Arg Arg Ile
    355                 360                 365
Glu Ala Glu Glu Leu Ser Leu Asp Ala Ser Glu Ile Val Ile Thr Ser
370                 375                 380
Thr Arg Gln Glu Ile Glu Glu Gln Trp Arg Leu Tyr Asp Gly Phe Asp
385                 390                 395                 400
Pro Val Leu Glu Arg Lys Leu Arg Ala Arg Ile Lys Arg Asn Val Ser
                405                 410                 415
Cys Tyr Gly Lys Phe Met Pro Arg Met Ala Ile Ile Pro Pro Gly Met
                420                 425                 430
Glu Phe His His Ile Val Pro Gln Asp Gly Asp Met Asp Gly Glu Thr
            435                 440                 445
Glu Gly Asn Glu Asp Asn Pro Ala Ser Pro Asp Pro Pro Ile Trp Ser
    450                 455                 460
Glu Ile Met Arg Phe Phe Thr Asn Pro Arg Lys Pro Val Ile Leu Ala
465                 470                 475                 480
Leu Ala Arg Pro Asp Pro Lys Lys Asn Ile Thr Thr Leu Val Lys Ala
                485                 490                 495
```

-continued

```
Phe Gly Glu Cys Arg Pro Leu Arg Glu Leu Ala Asn Leu Thr Leu Ile
            500                 505                 510
Asn Gly Asn Arg Asp Gly Ile Asp Glu Met Ser Ser Thr Ser Ala Ser
        515                 520                 525
Val Leu Leu Ser Val Leu Lys Leu Thr Asp Lys Tyr Asp Leu Tyr Gly
    530                 535                 540
Gln Val Ala Tyr Pro Lys His His Lys Gln Ser Gln Val Pro Glu Ile
545                 550                 555                 560
Tyr Arg Leu Ala Ala Lys Thr Lys Gly Val Phe Ile Asn Pro Ala Phe
                565                 570                 575
Ile Glu Pro Phe Gly Leu Thr Leu Ile Glu Ala Ala His Gly Leu
            580                 585                 590
Pro Ile Val Ala Thr Lys Asn Gly Gly Pro Val Asp Ile His Arg Val
            595                 600                 605
Leu Asp Asn Gly Leu Leu Val Asp Pro His Asp Gln Gln Ser Ile Ala
            610                 615                 620
Asp Ala Leu Leu Lys Leu Val Ala Gly Lys Gln Leu Trp Ala Arg Cys
625                 630                 635                 640
Arg Gln Asn Gly Leu Lys Asn Ile His Leu Phe Ser Trp Pro Glu His
                645                 650                 655
Cys Lys Thr Tyr Leu Ser Arg Ile Ala Gly Cys Lys Pro Arg His Pro
                660                 665                 670
Gln Trp Gln Arg Thr Asp Asp Gly Gly Glu Thr Ser Glu Ser Asp Ser
            675                 680                 685
Pro Gly Asp Ser Leu Arg Asp Ile Gln Asp Ile Ser Leu Asn Leu Lys
            690                 695                 700
Phe Ser Leu Asp Gly Glu Lys Ser Gly Ala Ser Gly Asn Asp Asp Ser
705                 710                 715                 720
Leu Asp Ser Glu Gly Asn Val Ala Asp Arg Lys Ser Arg Leu Glu Asn
                725                 730                 735
Ala Val Leu Ala Trp Ser Lys Gly Val Leu Lys Asp Thr Arg Lys Ser
            740                 745                 750
Gly Ser Thr Asp Lys Val Asp Gln Asn Thr Gly Ala Ala Lys Phe Pro
        755                 760                 765
Ala Leu Arg Arg Arg Lys His Ile Phe Val Ile Ser Val Asp Cys Asp
    770                 775                 780
Ser Thr Thr Gly Leu Leu Asp Ala Thr Lys Lys Ile Cys Glu Ala Val
785                 790                 795                 800
Glu Lys Glu Arg Thr Glu Gly Ser Ile Gly Phe Ile Leu Ser Thr Ser
                805                 810                 815
Met Thr Ile Ser Glu Ile His Ser Phe Leu Val Ser Gly His Leu Ser
                820                 825                 830
Pro Ser Asp Phe Asp Ala Phe Ile Cys Asn Ser Gly Ser Asp Leu Tyr
        835                 840                 845
Tyr Ser Thr Leu Asn Ser Glu Asp Gly Pro Phe Val Val Asp Phe Tyr
    850                 855                 860
Tyr His Ser His Ile Glu Tyr Arg Trp Gly Gly Glu Gly Leu Arg Lys
865                 870                 875                 880
Thr Leu Val Arg Trp Ala Ser Gln Val Thr Asp Lys Lys Ala Glu Ser
                885                 890                 895
Gly Glu Lys Val Leu Thr Pro Ala Glu Gln Leu Ser Thr Asn Tyr Cys
            900                 905                 910
```

-continued

```
Tyr Ala Phe Ser Val Gln Lys Pro Gly Met Thr Pro Val Lys Glu
    915                 920                 925

Leu Arg Lys Val Leu Arg Ile Gln Ala Leu Arg Cys His Val Ile Tyr
    930                 935                 940

Cys Gln Asn Gly Ser Arg Val Asn Val Ile Pro Val Leu Ala Ser Arg
945                 950                 955                 960

Ser Gln Ala Leu Arg Tyr Leu Tyr Leu Arg Trp Gly Val Glu Leu Ser
                965                 970                 975

Lys Met Val Val Phe Val Gly Glu Ser Gly Asp Thr Asp Tyr Glu Gly
                980                 985                 990

Leu Leu Gly Gly Val His Lys Thr Val Ile Leu Lys Gly Ile Cys Ser
                995                 1000                1005

Ser Ser Ser Asn Gln Ile His Ala Asn Arg Ser Tyr Pro Leu Ser Asp
    1010                1015                1020

Val Met Pro Ile Asp Ser Pro Asn Ile Val Gln Thr Pro Glu Asp Cys
1025                1030                1035                1040

Thr Thr Ser Asp Ile Arg Ser Ser Leu Glu Gln Leu Gly Leu Leu Lys
                1045                1050                1055

Val

<210> SEQ ID NO 3
<211> LENGTH: 343
<212> TYPE: PRT
<213> ORGANISM: Citrus unshiu

<400> SEQUENCE: 3

Gln Val Lys Tyr Val Val Glu Leu Ala Arg Ala Leu Gly Ser Met Pro
1               5                   10                  15

Gly Val Tyr Arg Val Asp Leu Leu Thr Arg Gln Val Ser Ala Pro Asp
                20                  25                  30

Val Asp Trp Ser Tyr Gly Glu Pro Thr Glu Met Leu Thr Pro Arg Asn
            35                  40                  45

Ser Asp Phe Met Asp Met Gly Glu Ser Ser Gly Ala Tyr Ile
        50                  55                  60

Ile Arg Ile Pro Phe Gly Pro Lys Asp Lys Tyr Ile Ala Lys Glu Leu
65                  70                  75                  80

Leu Trp Pro His Ile Pro Glu Phe Val Asp Gly Ala Leu Asn His Ile
                85                  90                  95

Ile Arg Met Ser Asn Val Leu Gly Glu Gln Ile Gly Gly Lys Pro
                100                 105                 110

Val Trp Pro Val Ala Ile His Gly His Tyr Ala Asp Ala Gly Asp Ser
            115                 120                 125

Ala Ala Leu Leu Ser Gly Ala Leu Asn Val Pro Met Leu Phe Thr Gly
    130                 135                 140

His Ser Leu Gly Arg Asp Lys Leu Glu Gln Leu Leu Lys Gln Ala Arg
145                 150                 155                 160

Leu Ser Arg Asp Glu Ile Asn Ala Thr Tyr Lys Ile Met Arg Arg Ile
                165                 170                 175

Glu Ala Glu Glu Leu Ser Leu Asp Ala Ser Glu Ile Val Ile Thr Ser
            180                 185                 190

Thr Arg Gln Glu Ile Glu Glu Gln Trp Arg Leu Tyr Asp Gly Phe Asp
        195                 200                 205

Pro Val Leu Glu Arg Lys Leu Arg Ala Arg Ile Lys Arg Asn Val Ser
    210                 215                 220
```

```
Cys Tyr Gly Lys Phe Met Pro Arg Met Ala Ile Ile Pro Pro Gly Met
225                 230                 235                 240

Glu Phe His His Ile Val Pro Gln Asp Gly Asp Met Asp Gly Glu Thr
                245                 250                 255

Glu Gly Asn Glu Asp Asn Pro Ala Ser Pro Asp Pro Pro Ile Trp Ser
            260                 265                 270

Glu Ile Met Arg Phe Phe Thr Asn Pro Arg Lys Pro Val Ile Leu Ala
        275                 280                 285

Leu Ala Arg Pro Asp Pro Lys Lys Asn Ile Thr Thr Leu Val Lys Ala
    290                 295                 300

Phe Gly Glu Cys Arg Pro Leu Arg Glu Leu Ala Asn Leu Thr Leu Ile
305                 310                 315                 320

Asn Gly Asn Arg Asp Gly Ile Asp Glu Met Ser Ser Thr Ser Ala Ser
                325                 330                 335

Val Leu Leu Ser Val Leu Lys
            340

<210> SEQ ID NO 4
<211> LENGTH: 341
<212> TYPE: PRT
<213> ORGANISM: Citrus unshiu
<220> FEATURE:
<223> OTHER INFORMATION: Xaa at position 109 is one of Ala, Arg, Asn,
      Asp, Cys, Gln, Glu, Gly, His, Ile, Leu, Lys, Met, Phe, Pro, Ser,
      Thr, Trp, Tyr, or Val

<400> SEQUENCE: 4

Gln Val Lys Tyr Val Val Glu Leu Ala Arg Ala Leu Ala Asn Thr Glu
1               5                   10                  15

Gly Val Tyr Arg Val Asp Leu Leu Thr Arg Gln Ile Ala Ser Pro Glu
                20                  25                  30

Val Asp Ser Ser Tyr Gly Glu Pro Asn Glu Met Leu Ser Cys Pro Ser
            35                  40                  45

Asp Gly Thr Gly Ser Cys Gly Ala Tyr Ile Ile Arg Ile Pro Cys Gly
        50                  55                  60

Ala Arg Asp Lys Tyr Ile Ala Lys Glu Ser Leu Trp Pro Tyr Ile His
65                  70                  75                  80

Glu Phe Val Asp Gly Ala Leu Asn His Ile Val Asn Met Ala Arg Ala
                85                  90                  95

Ile Gly Glu Gln Val Asn Gly Gly Lys Pro Thr Trp Xaa Tyr Val Ile
            100                 105                 110

His Gly His Tyr Ala Asp Ala Gly Glu Val Ala Gly His Leu Pro Gly
        115                 120                 125

Gly Leu Asn Val Pro Met Val Leu Thr Gly His Ser Leu Gly Arg Asn
    130                 135                 140

Lys Phe Glu Gln Leu Leu Lys Gln Gly Arg Leu Pro Lys Asn Ile Asn
145                 150                 155                 160

Ala Ser Tyr Lys Ile Met Arg Arg Phe Glu Ala Glu Leu Gly Leu
                165                 170                 175

Asp Ala Ser Glu Met Val Val Thr Ser Thr Arg Gln Glu Ile Glu Met
            180                 185                 190

Gln Trp Gly Leu Tyr Asp Gly Phe Asp Leu Lys Leu Glu Arg Lys Leu
        195                 200                 205

Arg Val Arg Arg Gln Arg Gly Val Ser Cys Phe Gly Arg Phe Met Pro
    210                 215                 220

Arg Met Val Val Ile Pro Pro Gly Met Asp Phe Ser Tyr Val Thr Thr
```

```
225                 230                 235                 240

Gln Asp Thr Met Gly Gly Asp Thr Asp Leu Lys Ser Leu Ile Val Asn
                245                 250                 255

Asp Arg Thr Gln Thr Thr Arg Asn Leu Pro Pro Met Trp Ser Glu Val
            260                 265                 270

Met Arg Phe Phe Thr Asn Pro His Lys Pro Thr Ile Leu Ala Leu Ser
        275                 280                 285

Arg Pro Asp Pro Lys Lys Asn Val Thr Thr Leu Leu Lys Ala Phe Gly
    290                 295                 300

Glu Cys Gln Pro Leu Arg Glu Leu Ala Asn Met Thr Leu Ile Leu Gly
305                 310                 315                 320

Asn Arg Asp Asp Ile Glu Asp Met Ser Asn Ser Ser Ser Val Val Leu
                325                 330                 335

Thr Thr Val Leu Asn
                340

<210> SEQ ID NO 5
<211> LENGTH: 348
<212> TYPE: PRT
<213> ORGANISM: Citrus unshiu

<400> SEQUENCE: 5

Gln Ile Lys Tyr Val Val Glu Leu Ala Arg Ala Leu Ala Arg Met Pro
  1               5                  10                  15

Gly Val Tyr Arg Val Asp Leu Phe Ser Arg Gln Val Ser Ser Pro Glu
                 20                  25                  30

Val Asp Trp Ser Tyr Gly Glu Pro Ala Glu Met Leu Thr Gly Gly Pro
             35                  40                  45

Glu Asp Asp Gly Ile Glu Val Gly Glu Ser Ser Gly Ala Tyr Ile Ile
     50                  55                  60

Arg Ile Pro Phe Gly Pro Arg Asp Lys Tyr Leu Arg Lys Glu Leu Leu
 65                  70                  75                  80

Trp Pro Tyr Ile Gln Glu Phe Val Asp Gly Ala Leu Ala His Cys Leu
                 85                  90                  95

Asn Met Ser Lys Val Leu Gly Glu Gln Ile Gly Gly Gln Pro Val
                100                 105                 110

Trp Pro Tyr Val Ile His Gly His Tyr Ala Asp Ala Gly Asp Ser Ala
            115                 120                 125

Ala Leu Leu Ser Gly Ala Leu Asn Val Pro Met Val Leu Thr Gly His
        130                 135                 140

Ser Leu Gly Arg Asn Lys Leu Glu Gln Leu Leu Lys Gln Gly Arg Gln
145                 150                 155                 160

Ser Lys Glu Asp Ile Asn Ser Thr Tyr Lys Ile Met Arg Arg Ile Glu
                165                 170                 175

Gly Glu Glu Leu Ser Leu Asp Ala Ala Glu Leu Val Ile Thr Ser Thr
            180                 185                 190

Lys Gln Glu Ile Asp Glu Gln Trp Gly Leu Tyr Asp Gly Phe Asp Val
        195                 200                 205

Lys Leu Glu Lys Val Leu Arg Ala Arg Ala Arg Arg Gly Gly Asn Cys
    210                 215                 220

His Asp Arg Tyr Met Pro Arg Met Val Ile Pro Pro Gly Met Asp
225                 230                 235                 240

Phe Ser Asn Val Val Ala Gln Glu Asp Thr Pro Glu Val Asp Gly Glu
                245                 250                 255
```

Leu Thr Ser Leu Ile Gly Gly Thr Asp Gly Ser Ser Pro Lys Ala Ile
        260                 265                 270

Pro Ala Ile Trp Ser Asp Val Met Arg Phe Leu Thr Asn Pro His Lys
        275                 280                 285

Pro Met Ile Leu Ala Leu Ser Arg Pro Asp Pro Lys Lys Asn Ile Thr
        290                 295                 300

Thr Leu Leu Lys Ala Phe Gly Glu Cys Arg Pro Leu Arg Glu Phe Ala
305                 310                 315                 320

Asn Leu Thr Leu Ile Met Gly Asn Arg Asp Asp Ile Glu Glu Met Ser
                325                 330                 335

Ser Gly Asn Ala Ser Val Leu Ile Thr Val Leu Lys
                340                 345

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 6
gattctgata caggtgg                                                      17

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 7
tacagatcat acttgtcaat ca                                                22

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 8
gaagaagatg gcaggaaacg attgg                                             25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:synthetic
      DNA

<400> SEQUENCE: 9
ccgatagcag caacaagaca tcgag                                             25

<210> SEQ ID NO 10
<211> LENGTH: 343
<212> TYPE: PRT
<213> ORGANISM: Spinacia sp.

<400> SEQUENCE: 10

Gln Val Lys Tyr Val Val Glu Leu Ala Arg Ala Leu Gly Ser Met Pro

-continued

```
  1               5                    10                   15
Gly Val Tyr Arg Val Asp Leu Leu Thr Arg Gln Val Ser Ala Pro Gly
            20                   25                  30

Val Asp Trp Ser Tyr Gly Glu Pro Thr Glu Met Leu Ser Ser Arg Asn
            35                   40                  45

Ser Glu Asn Ser Thr Glu Gln Leu Gly Glu Ser Ser Gly Ala Tyr Ile
        50                   55                  60

Ile Arg Ile Pro Phe Gly Pro Lys Asp Lys Tyr Val Ala Lys Glu Leu
 65                      70                   75                  80

Leu Trp Pro Tyr Ile Pro Glu Phe Val Asp Gly Ala Leu Ser His Ile
                85                   90                  95

Lys Gln Met Ser Lys Val Leu Gly Glu Gln Ile Gly Gly Gly Leu Pro
            100                  105                 110

Val Trp Pro Ala Ser Val His Gly His Tyr Ala Asp Ala Gly Asp Ser
            115                  120                 125

Ala Ala Leu Leu Ser Gly Ala Leu Asn Val Pro Met Val Phe Thr Gly
 130                     135                  140

His Ser Leu Gly Arg Asp Lys Leu Asp Gln Leu Leu Lys Gln Gly Arg
 145                     150                  155                 160

Leu Ser Arg Glu Glu Val Asp Ala Thr Tyr Lys Ile Met Arg Arg Ile
            165                  170                 175

Glu Ala Glu Glu Leu Cys Leu Asp Ala Ser Glu Ile Val Ile Thr Ser
            180                  185                 190

Thr Arg Gln Glu Ile Glu Glu Gln Trp Gln Leu Tyr His Gly Phe Asp
            195                  200                 205

Leu Val Leu Glu Arg Lys Leu Arg Ala Arg Met Arg Arg Gly Val Ser
        210                  215                 220

Cys His Gly Arg Phe Met Pro Arg Met Ala Lys Ile Pro Pro Gly Met
 225                     230                  235                 240

Glu Phe Asn His Ile Ala Pro Glu Asp Ala Asp Met Asp Thr Asp Ile
                245                  250                 255

Asp Gly His Lys Glu Ser Asn Ala Asn Pro Asp Pro Val Ile Trp Ser
                260                  265                 270

Glu Ile Met Arg Phe Phe Ser Asn Gly Arg Lys Pro Met Ile Leu Ala
            275                  280                 285

Leu Ala Arg Pro Asp Pro Lys Lys Asn Leu Thr Thr Leu Val Lys Ala
        290                  295                 300

Phe Gly Glu Cys Arg Pro Leu Arg Glu Leu Ala Asn Leu Thr Leu Ile
 305                     310                  315                 320

Ile Gly Asn Arg Asp Asp Ile Asp Glu Met Ser Thr Thr Ser Ser Ser
                325                  330                 335

Val Leu Ile Ser Ile Leu Lys
            340
```

SUCROSE PHOSPHATE SYNTHASE FROM CITRUS AND DNA ENCODING THE SAME

BACKGROUND OF THE INVENTION

1. Technical Field

The present invention relates to a sucrose phosphate synthase from Citrus including its isoform, and to DNA encoding the enzyme.

2. Earlier Technology

Sucrose is a transport form of the photoassimilate in most plants. The sucrose in mature leaves (source) is mostly transported by the phloem to the plant organs (sink) that are net consumers of the photo-assimilate. A key enzyme of sucrose synthesis pathway, sucrose-phosphate synthase (EC 2.4.1.14) (hereinafter referred to as "SPS"), catalyzes the following reaction:

Fructose 6-phosphate+UDP glucose→Sucrose 6-phosphate+UDP Sucrose 6-phosphate is converted to sucrose by sucrose phosphatase.

Considerable interest has focused on the role of SPS in regulation of sucrose synthesis in source leaves (Kerr, P. S. and Huber, S. C. (1987) Planta 170:197–204; and Echeverria, E. and Burns, J. K. (1989) Plant Physiol. 90:530–533). SPS activity itself has been found in many plants, for example cucurbits (Lingle, S. E. and Dunlap, J. R. (1987) Plant Physiol. 84:386–389; Hubbard, N. L. et al. (1989) Plant Physiol. 91:1527–1534; and Burger, Y. and Schaffer, A. A. (1991) Sucrose metabolism in mature fruit peduncles of *Cucumis melo* and *Cucumis sativus*. In:Recent advances in phloemtransport and assimilate partitioning, pp. 244–247, Bonnemain, J. L. et al. eds. ouest Editions, Nantes, France), peach (Hubbard, N. L. et al. (1991) Physiol. Plant 82:191–196), pear (Moriguchi, T. et al. (1992) J. Am. Soc. Hortic. Sci. 117:247–278), and celery (Stoop, J. M. H. and Pharr, D. M. (1994) J. Am. Soc. Hortic. Sci. 119:237–242), sugar beet (Fieuw, S. and Willenbrink, J. (1987) J. Plant Physiol. 131:153–162), sugar cane (Wendler, R. et al. (1990) Planta 183:31–39; and Goldner, W. et al. (1991) Plant Sci. 73:143–147), sucrose-accumulating Lycopersicon spp. (Miron, D. and Schaffer, A. A. (1991) Humb. And Bonpl. Plant Physiol. 95:623–627), Dali, N. et al. (1992) Plant Physiol. 99:434–438; and Stommel, J. R. (1992) Plant Physiol. 99:324–328), rice (Smyth, D. A. and Prescott, H. E. (1989) Plant Physiol. 89:893–896), strawberry (Hubbard, N. L. et al. (1991) Physiol. Plant 82:191–196), and citrus (Lowell, C. A. et al. (1989) Plant Physiol. 90:1394–1402; and Echeverria, E. (1992) Plant Sci. 85:125–129).

To investigate the enzymatic function of SPS on sucrose biosynthesis, SPS has been purified to near homogeneity from spinach (Salvucci, M.E. et al. (1990) Arch. Biochem. Biophys. 281:212–218), wheat (Salerno, G. L. et al. (1991) Physiol. Plant 81:541–547), and maize (Bruneau, J. -M. et al. (1991) Plant Physiol. 96:473–478). SPS is an allosteric enzyme which is activated by binding of the substrate-similar glucose-6-phosphate and inhibited by $P_i$ at the allosteric site (Doehlert, D. C. and Huber, S. C. (1983) Plant Physiol. 73:989–994). In addition, the activity of SPS is regulated by protein phosphorylation (Huber, J. L. A. et al. (1989) Arch. Biochem. Biophys. 270:681–690; Siegl, G. et al. (1990) FEBS Letters 270:198–202; and Huber, S. C. and Huber J. L. (1991) Plant Cell Physiol. 32:319–326). Recently, the function and structure of SPS have also been studied at the molecular level in maize (Worrell, A. C. et al. (1991) Plant Cell 3:1121–1130), spinach (Klein, R. R. et al. (1993) Planta 190:498–510), and sugar beet (Hesse, H. et al. (1995) Mol. Gen. Genet. 247:515–520).

In citrus, the sucrose accumulation is one of the very important events in fruit development. Phloem-free juice sacs at the middle stage of fruit development showed higher SPS activity than the adjacent transport tissues, vascular nodules and segment epidermis (Lowell, C. A. et al. (1989) Plant Physiol. 90:1394–1402). However, analysis of the function and expression of SPS at the molecular level has been quite limited in Citrus.

An object of this invention is to clone cDNA for SPS from Citrus and characterize it at the molecular level.

Another object of the invention is to provide an SPS from Citrus.

SUMMARY OF THE INVENTION

This invention provides DNA encoding a sucrose phosphate synthase from Citrus having an amino acid sequence shown in SEQ ID NO:2, or an isoform thereof sharing at least 50% homology with said sucrose phosphate synthase in amino acid level.

In a preferred embodiment of the invention, the isoform is a different type of sucrose phosphate synthase from Citrus, containing a partial amino acid sequence shown in SEQ ID NO:4 or SEQ ID NO:5.

In another embodiment, the DNA has a nucleotide sequence shown in SEQ ID NO:1 that encodes the mature form of the sucrose phosphate synthase.

This invention further provides a sucrose phosphate synthase from Citrus or an isoform thereof, as defined above.

BRIEF DESCRIPTION OF THE DRAWINGS

FIG. 2 shows a comparison of the deduced amino acid sequences of three partial SPS cDNAs obtained by RT-PCR (pSPS1(SEQ ID NO:3), pSPS2 (SEQ ID NO:4) and pSPS3 (SEQ ID NO:5)) with the amino acid sequence of spinach SPS (SEQ ID NO:10) (SoSPS). Identical amino acid residues with respect to pSPS1 are shown as dots and gaps as dashes.

FIGS. 3A and 3B show nucleotide (SEQ ID NO:1) and amino acid sequences (SEQ ID NO:2) of the CitSPS1 cDNA. The numerical numbers on the right correspond to nucleotide numbers.

FIGS. 4A and 4B show a comparison of the deduced amino acid sequence encoded by CitSPS1 with sequences from maize (ZmSPS), spinach (SoSPS) and sugar beet (BvSPS1). Identical residues are shown as dots and gaps as dashes. The amino acid $Ser^{198}$, determined to be a regulatory phosphorylation site for spinach SPS, is indicated by a double underline. The RXXSV consensus site for CaM-dependent protein kinase II and phosphoylase kinase ($Arg^{147}$-$Ile^{148}$-$Ser^{149}$-$Ser^{150}$-$Val^{151}$) (amino acids 147–151 of (SEQ ID NO:2) is indicated by a single underline.

PREFERRED EMBODIMENTS OF THE INVENTION

Figure 1:
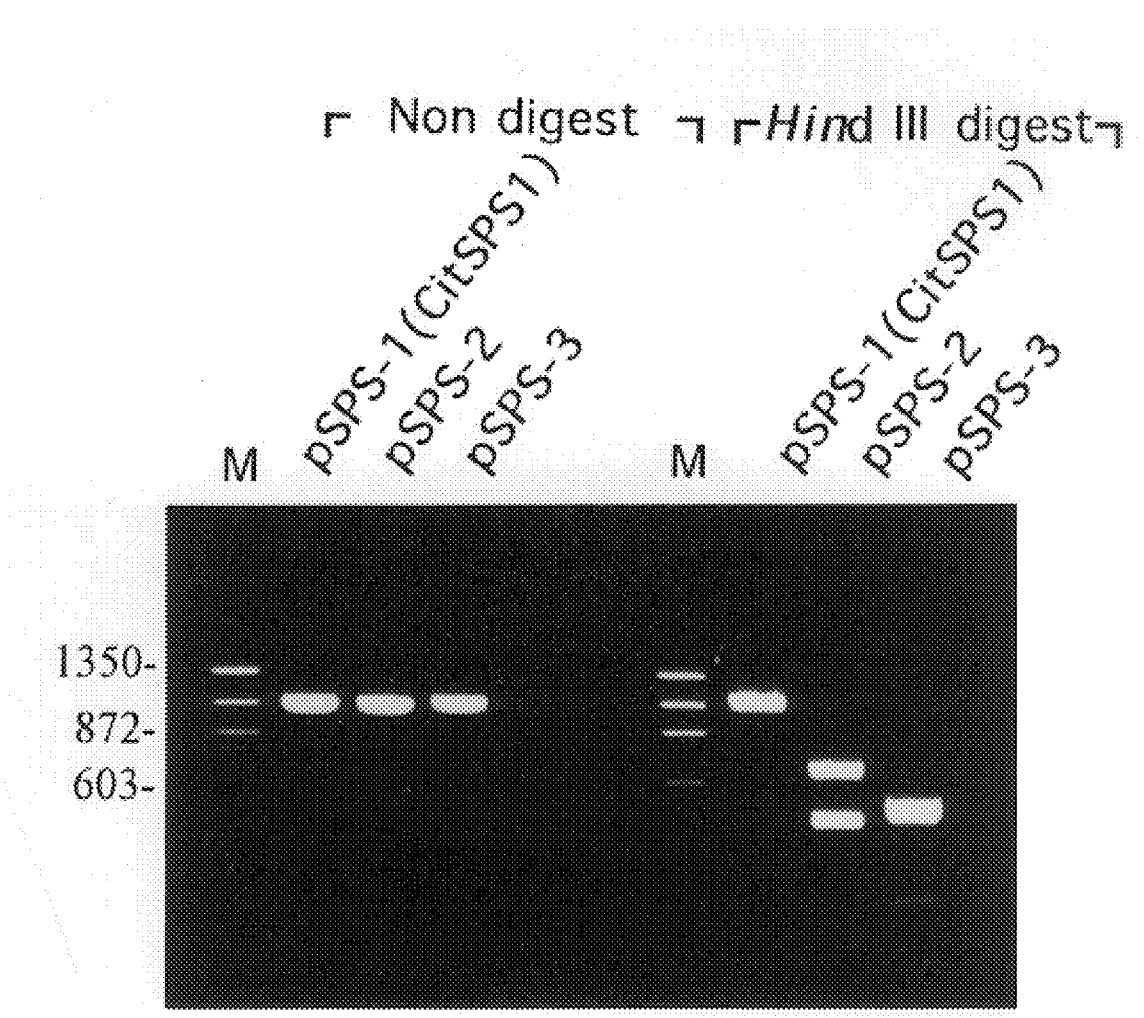
FIG. 1 shows insert and Hind III restriction fragment patterns of three partial clones, i.e. pCPS-1 (CitSPS1), pSPS-2 and pSPS-3, encoding different SPS isoforms from *Citrus unshiu* Marc. obtained by RT-PCR. M is a øX174/Hae III digest as molecular weight marker.

According to this invention, there are provided a sucrose phosphate synthase from Citrus and an isoform thereof wherein the sucrose phosphate synthase has an amino acid sequence shown in SEQ ID NO:2, and the isoform shares at least 50%, particularly at least 60%, homology with the sucrose phosphate synthase (SEQ ID NO:2) in amino acid level.

The sucrose phosphate synthase and its isoform of the invention may be purified directly from a citrus plant or synthesized by the DNA recombinant technology (see below).

The term "isoform" used herein is intended to include any analog of the sucrose phosphate synthase having an amino acid sequence shown in SEQ ID NO:2, provided that the analog is derived from Citrus and bears a sucrose phosphate synthase activity. In an preferred embodiment, the isoform includes ones containing partial amino acid sequences shown in SEQ ID NO:4 and SEQ ID NO:5.

Furthermore, the term "Citrus" used herein refers to any class of plants belonging to Citrus.

It is known that the sucrose phosphate synthase is an enzyme important for sucrose synthesis in plants and associated with the accumulation of sugar, and it catalyzes the reaction: fructose 6-phosphate+UDP glucose→sucrose 6-phosphate+UDP (see "Background of the Invention"). Thus, by the sucrose phosphate synthase activity is meant an activity catalyzing the above reaction.

This invention further provides DNA encoding a sucrose phosphate synthase having an amino acid sequence shown in SEQ ID NO:2 or an isoform thereof as defined above. An exemplary nucleotide sequence of the DNA has 26-3196 nucleotides shown in SEQ ID NO:1 or FIG. 3 that encode the mature form of the sucrose phosphate synthase of SEQ ID NO:2.

The cloning of SPS CDNA of the invention can be performed as follows, from any tissues or organs of Citrus, for example leaves, flowers, fruits, and roots.

Total RNA is separated from Citrus tissues or organs, and poly(A) $^+$RNA can subsequently be isolated from the total RNA by using an oligo(dt) cellulose column. To prepare a cDNA library, the obtained poly(A) $^+$RNA is treated with a reverse transcryptase by the oligo(dT) primer method or randomly primed cDNA synthesis to form CDNA whose double stranded cDNA is cloned into a phage vector. As the phage vector, λ-phages such as M13 can normally be used. For screening of SPS cDNA clones, the phages can be amplified in bacteria such as *Escherichia coli,* through infection, after which cDNA clones of interest are selected by routine hybridization or immunoassays or measurement of SPS activity. The cloning methods that are taught by, for example, Sambrook, J. et al. in "Molecular Cloning: A Laboratory Manual," Cold Spring Harbor Press (1989) can be used in cloning of SPS CDNA from Citrus plants.

Through the above mentioned methods, we could obtain three different partial cDNA clones from *Citrus unshiu* Marc. fruits or leaves by the reverse transcriptase-polymerase chain reaction (RT-PCR) using sense and antisense primers synthesized on the basis of a conserved region of the SPS CDNA sequences of maize and spinach. After reamplification, the three partial cDNA clones having a uniform length of approximately 1030 bp are isolated and designated as pSPS1, pSPS2 and pSPS3, respectively. They share an about 65–70% homology with each other, and in comparison with the amino acid sequence of spinach SPS, the pSPS1, pSPS2 and pSPS3 share homologies of 82.2%, 64.1% and 70.5%, respectively, with the spinach SPS in amino acid level (see FIG.2). From the homology comparison, the obtained clones are confirmed to be clearly the partial cDNA clones of SPS.

The full length SPS CDNA clone can be obtained by repeating the above mentioned cloning methods while using any one of the three different SPS cDNA clones, pSPS1, pSPS2 and pSPS3, as a probe. The selection of the cDNA clone of interest can be performed by utilizing either a hybridization using all or part of pSPS1, pSPS2 or pSPS3 as a probe under stringent or low or non-stringent conditions (e.g., Frohman, M. A. Acad. Sci. USA, 85:8998–9002 (1988)), or an immunoassay using a monoclonal or polyclonal anti-SPS antibody (e.g., Young, R. A. and Davis, R. W., Proc. Natl. Acad. Sci. USA, 80:1194–1198 (1983)). The hybridization conditions are well known to an ordinary skilled person in the art, as well as the preparation of monoclonal or polyclonal antibodies. As the probe, degenerate oligonucleotide probes of at least 17–20 nucleotides can be normally employed. The sequencing of the selected cDNA is carried out by the conventional methods such as Sanger-Coulson method (J. Mol. Biol., 143:161–178 (1980)) and Maxam-Cilbert method (Proc. Natl. Acad. Sci. USA, 74:560–564 (1977)).

One of the full length SPS cDNAs, which is named CitSPS1, is 3539 bp in length with an open reading frame encoding a 117.8 KDa SPS protein with 1057 amino acids (see SEQ ID NO:1 and FIG. 3). The deduced amino acid sequence of CitSPS1 is shown in SEQ ID NO:2. The homology of the amino acid sequence of CitSPS1 with those of SPS of maize And spinach is 55.8% and 74%, respectively (see FIG. 4). From comparison of amino acid sequences, the major phosphorylation site in CitSPS1 is conserved as $Ser^{150}$ while that in spinach SPS is $Ser^{158}$, the site also fitting the RXXSV consensus sequence for CaM-dependent protein kinase II and phosphorylase kinase sites, i.e. $Arg^{147}$-Ile-Ser-Ser-$Val^{151}$ (amino acids 147–151 of SEQ ID NO:2). Additionally, the phosphorylated serine has acidic residues on its C-terminal side ($Asp^{152}$, $Glu^{155}$) which is in common in casein kinase II sites. These features are in agreement with the data obtained for spinach SPS and the amino acid sequence deduced from sugar beet SPS CDNA (Hesse, H. et al., Mol. Gen. Genet. 247:515–520 (1995), indicating that CitSPS1 represents a full length cDNA for SPS in citrus.

Similarly, full length CitSPS2 and CitSPS3 DNAs can be prepared through screening using pSPS2 or pSPS3, respectively, as a probe under stringent hybridization conditions. By Northern blot analysis of total RNA from various citrus tissues (e.g., leaves, flowers and fruits), the presence of SPS mRNA can be identified (see FIG. 6). And, through genetic analysis using RFLP between *C. unshiu* cv. Miyagawa wase and *C. sinensis* cv. Trovita, it has now been found that the three SPS genes are not allele from the same locus, but different loci respectively. When the pSPS1, pSPS2 or pSPS3 is used as a probe in hybridization under low or non-stringent conditions, other isoforms will also be identified and isolated in the similar manners. As seen in FIG. 4, there exist several highly conserved regions between different isoforms, and on the basis of sequences of the regions, suitable probes can easily be prepared.

Once an SPS cDNA of interest is obtained, it is treated with restriction enzymes and then cloned into an appropriate expression vector pretreated with the same enzymes. The expression vector may contain a promoter region, a selectable marker(s), an origin of replication, an appropriate restriction sites to introduce an SPS CDNA, an initiation codon ATG, a terminator, and a ribosome binding site. As the promoter, exemplified are lac promoter, trp promoter, tac promoter, $\lambda R_L$ promoter, and so forth. The selectable marker may be for example drug resistance genes such as tetracycline resistance gene ($TC^R$), ampicillin resistance gene ($AP^R$), streptomycin resistance gene, and kanamycin resistance gene.

After insertion, an appropriate host cell is transformed with the expression vector. The host cell may include prokaryotic cells, particularly bacterial cells such as *Escherichia coli* and Bacillus species. For *E coli* strains, the expression vectors used may be pBR (e.g., pBR322) plasmids, pUC plasmids, pBH plasmids, pSom plasmids, etc. For Bacillus strains, pBD and pSL plasmids may be used as expression vectors (Gryczan, T. et al. (1980b) J. Bacteriol. 141:246–253; and Keggins, K. M. et al. (1979) J. Bacteriol., 139:1001–1006). Normally, as the expression vector is preferred a plasmid containing a polylinker to insert a foreign gene therein. When the plasmid vector is introduced into a host cell, it may be mixed with the host cell in the presence of calcium chloride and then subjected to heat shock; or alternatively electroporation may be used. Thereafter, the transformed cells are cultivated in a nutrient culture medium under such conditions that the SPS cDNA can be expressed under control of a promoter.

In summary, the preparation of the SPS or its isoforms of the invention can be performed by the method which comprises the following steps of:

introducing a full length SPS cDNA into an appropriate expression vector;

transforming an appropriate host cell with the obtained expression vector;

cultivating the transformed host cell in an appropriate nutrient culture medium under such conditions that the SPS CDNA can be expressed under control of a promoter; and recovering the SPS from the cell culture.

It is apparent to a skilled person that the expression of an SPS CDNA may alternatively be performed in a transformant eukaryotic cell such as yeast cell.

The recovery of the SPS of interest can be performed by combining conventional methods such as ion-exchange chromatography, hydrophobic interaction chromatography, affinity chromatography, gel filtration chromatography, reverse phase HPLC, ethanol or ammonium sulfate precipitation, etc.

In the cloning and expression of an SPS CDNA as described above, various known procedures can be utilized, such as ones described in Sambrook, J. et al. (supra) and in Ausubel, F. M. et al. ed. in "Current Protocols in Molecular Cloning" Greene Publishing and Wiley Interscience, NY, 1989.

Alternatively, the SPS and its isoforms of this invention may be purified directly from Citrus tissues and organs by, for example, any combinations of the chromatographies as described above. Effective purification will be able to be performed by use of an immune column to which an anti-SPS antibody has been covalently attached.

This invention will further be illustrated by the following non-limited Examples in more detail.

EXAMPLES

Plant Materials

In the Examples set forth below, *Citrus unshiu* Marc. was used as a plant material, but it should be understood that this invention is not limited thereto.

Example 1

Amplification by RT-PCR using mRNA from Leaf and Fruit

Total RNA was isolated from fruits (particularly, juice sacs and pulp segments) or leaves of *C. unshiu* by a modification of the single-step method (Chomczynski, P. and Sacchi, N. (1987) Anal. Biochem. 162:156–159). Poly (A) $^+$RNA was purified from the total RNA with an Oligotex™ Kit (Takara, Japan). First-strand CDNA was synthesized from the poly(A) $^+$RNA using a First-Strand cDNA synthesis Kit™ (Pharmacia). PCR was performed on the first-strand CDNA using the following cycle conditions: 1 min at 94° C. (annealing), 1 min at 50° C. (denaturation), and 2 min at 72° C. (extension). For the PCR reaction, the sense primer (SPSIF: 5'-GATTCTGATACAGGTGG-3' (SEQ ID NO:6)) and antisense primer (SPS2R: 5'-TACAGATCATACTTGTCAATCA-3' (SEQ ID NO:7)) were synthesized on the basis of the sequence of a region of SPS genes that is conserved in maize and spinach. The amplified fragments were cloned into the PCRII vector with the TA Cloning System Kit™ (Invitrogen). To confirm the identity of the amplified products, the plasmid inserts were amplified by PCR with the same primers (SPSIF and SPS2R) and mapped with several restriction enzymes.

The RT-PCR products were cloned into the pCRII vector, by which 30 clones were isolated. After amplification of the inserts in the 30 isolated clones by PCR, three different amplification products with a length of approximately 1030 bp but with different restriction patterns were obtained (FIG. 1). These clones were named pSPS1, pSPS2 and pSPS3. They were sequenced and compared with each other with respect to homology in their amino acid sequences. As a result, they shared about 65–70% homology although their homology level was particularly low at the amino acid positions from 250 to 280 (FIG. 2). The amino acid sequences encoded by pSPS1, pSPS2 and pSPS3 (SEQ ID NOS:3, 4 and 5, respectively) also showed similarity to that of spinach SPS at the level of 82.2%, 64.1% and 70.5% identity, respectively, suggesting that these clones were the partial cDNA clones of SPS.

Example 2

1. Construction and Screening of a CDNA Library From Citrus Fruit

The CDNA Synthesis Kit™ (Pharmacia) was used to synthesize cDNA from poly(A)RNA of citrus fruits (juice sacs and pulp segments) harvested 124 days after anthesis, which was then ligated into a λ-ZAPII cloning vector and packaged with Gigapack II Gold Packaging Extract™ (Stratagene). The phages were amplified in the *Escherichia coli XL*-1-Blue MRF' strain. Approximately $2.6 \times 10^5$ pfu of the fruit cDNA library was screened with one of three partial SPS cDNA by the ECL nucleic acid labelling and detection system (Amersham). The filters were washed twice for 20 min each in 6 M urea-0.2×SSC-0.1% SDS at 42° C. The nucleotide sequences were determined with a Taq Dye Terminator Cycle Sequencing Kit™ (Applied Biosystems) and analyzed with GENETYX software (Software Development)

2. Cloning and Sequencing of CitSPS1 Genomic DNA

Genomic clone of CitSPS1 was isolated by PCR using shuttle method. PCR was performed on the genomic DNA and LA Taq polymerase (TaKaRa, Japan) using the following cycle conditions: 1 min at 94° C., 1 min at 50° C. and 4 min 68° C. for 30 cycles. For the PCR reaction, the sense primer (SPS-full-F 5'-GAAGAAGATGGCAGGAAACGATTGG-3' (SEQ ID NO:8)) and antisense primer (SPS-full-R 5'-CCGATAGCAGCAAGACATCGAG-3' (SEQ ID NO:9)) were synthesized on the basis of 5' and 3' regions of CitSPS1 CDNA sequence by using DNA synthesizer-1000 (BECKMAN). The amplified fragments were cloned into the pCRII vector with TA Cloning System Kit™ (Invitrogen). The nucleotide sequences were determined with a Taq Dye Terminator Cycle Sequencing FS Kit™ (Parkin-Elmer) and analyzed with GENETYX software ver. 8.0 (Software Development).

By screening the cDNA library from fruit poly(A) $^+$RNA in λ-ZAPII using one of the three SPS partial cDNAs as a probe, one clone named CitSPS1 was obtained and proved to contain a full length cDNA. This cDNA was 3539 bp in length with an open reading frame encoding 1057 amino acids, corresponding to a protein with a predicted molecular weight of 117.8 kDa (FIG. 3). The 3539 bp nucleotide sequence and 1057 amino acid sequences of the CitSPS1 are shown as SEQ ID NOS:1 and 2, respectively. The homology of the deduced amino acid sequence of CitSPS1 with those of SPS of maize and spinach was 55.8% and 74%, respectively (FIG. 4).

In addition, it has been found that the major phosphorylation site in spinach SPS, $Ser^{158}$, as determined by trypsin digestion (McMichael R. W. et al. (1993) Arch. Biochem. Biophys. 307:248–252) is conserved as $Ser^{150}$ in CitSPS1, and the site also fits the RXXSV consensus sequence for CaM-dependent protein kinase II and phosphorylase kinase ($Arg^{147}$-Ile-Ser-Ser-$Val^{151}$ (amino acids 147–151 of SEQ ID NO:2)). Furthermore, the phosphorylated serine has acidic residues on its C-terminal side ($Asp^{152}$, $Glu^{155}$) which is in common in casein kinase II sites. These features are in agreement with the data obtained for spinach SPS and the amino acid sequence deduced from sugar beet SPS CDNA (Hesse H. et al. (1995) Mol. Gen. Genet. 247:515–520), confirming that CitSPS1 represents a full length cDNA for SPS in citrus.

Example 3

Genomic DNA Blot Analysis

Genomic DNA was isolated from mature leaves of C. unshiu according to Dellaporta, S. L. et al. (1983) Plant Mol. Biol. Rep. 1:19–21. The genomic DNA (10 μg) was digested with Dra I, EcoR I and Hind III and fractionated by electrophoresis on 0.7% (w/v) agarose gel;, then transferred to a nylon membrane (Hybond-N, Amersham). The blot was hybridized with the CitSPS1 insert DNA labeled with Dig-11-dUTP and a random primer DNA labeling kit™ (Boehringer Mannheim), and was washed twice in 0.2×SSC and 0.1% SDS at 65° C. for 20 min and then exposed to X-ray film (RX; Fuji).

Figure 5:
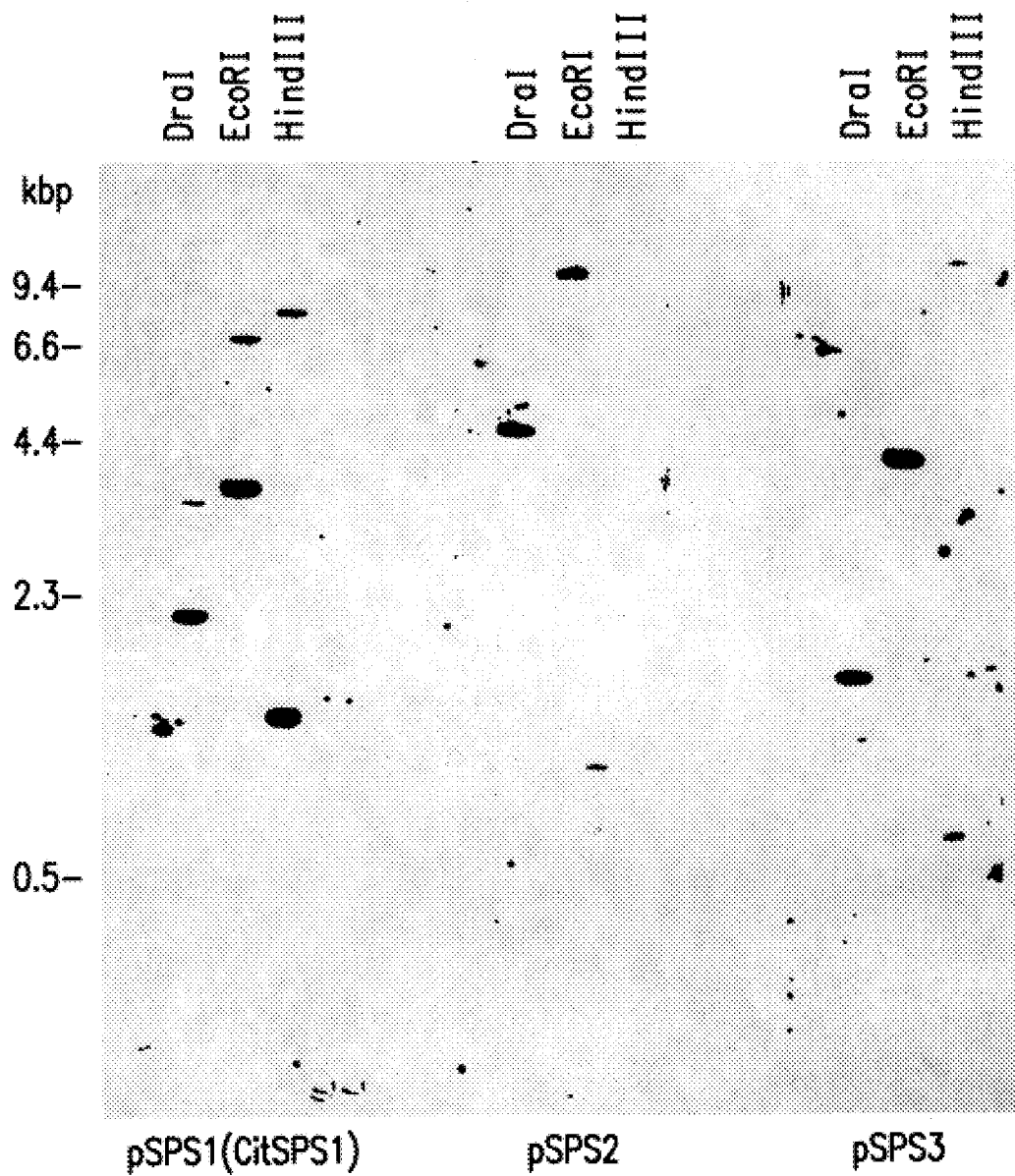
FIG. 5 shows a Southern blot analysis of DNA. from citrus using pSPS1, pSPS2 or pSPS3 as probes. Genomic DNA (10 μg) was digested with Dra I, EcoR I or Hind III, fractionated by electrophoresis of 0.7% (w/v) agarose gel, and transferred to the Hybond-N membrane.

As shown in FIG. 5, only a few fragments hybridized when the CitSPS1 probe was used on total genomic DNA digested with Dra I, EcoR I or Hind III. The hybridization patterns obtained with the other types of partial clones (pSPS2 and pSPS3) were completely different from those seen with CitSPS1. These results suggested that there exist several different types of SPS proteins in a Citrus species and that each of the SPS clones is represented by a small gene family in citrus genome.

Example 4

Northern Blot Analysis

The expression profiles of the three SPS genes were studied by Northern blot analysis of total RNA prepared from young leaves, mature leaves, flowers, immature and mature fruits, using the partial cDNA clones pSPS1, pSPS2 and pSPS3 as probes.

Total RNA was isolated from citrus young leaves, mature leaves, flowers, immature fruits, or mature fruits harvested 66 and 171 days after anthesis. Total RNA (10 μg aliquot) was electrophoresed on a 1.0% agarose gel containing formaldehyde (Ausbel, F. M. et al. (1987) in "Current Protocols in Molecular Biology," John Wiley and Sons, New York) and then transferred to the Hybond-N (Amersham). Hybridization was carried out under the stringent conditions as described in Example 3. The results are shown in FIG. 6.

Figure 6:
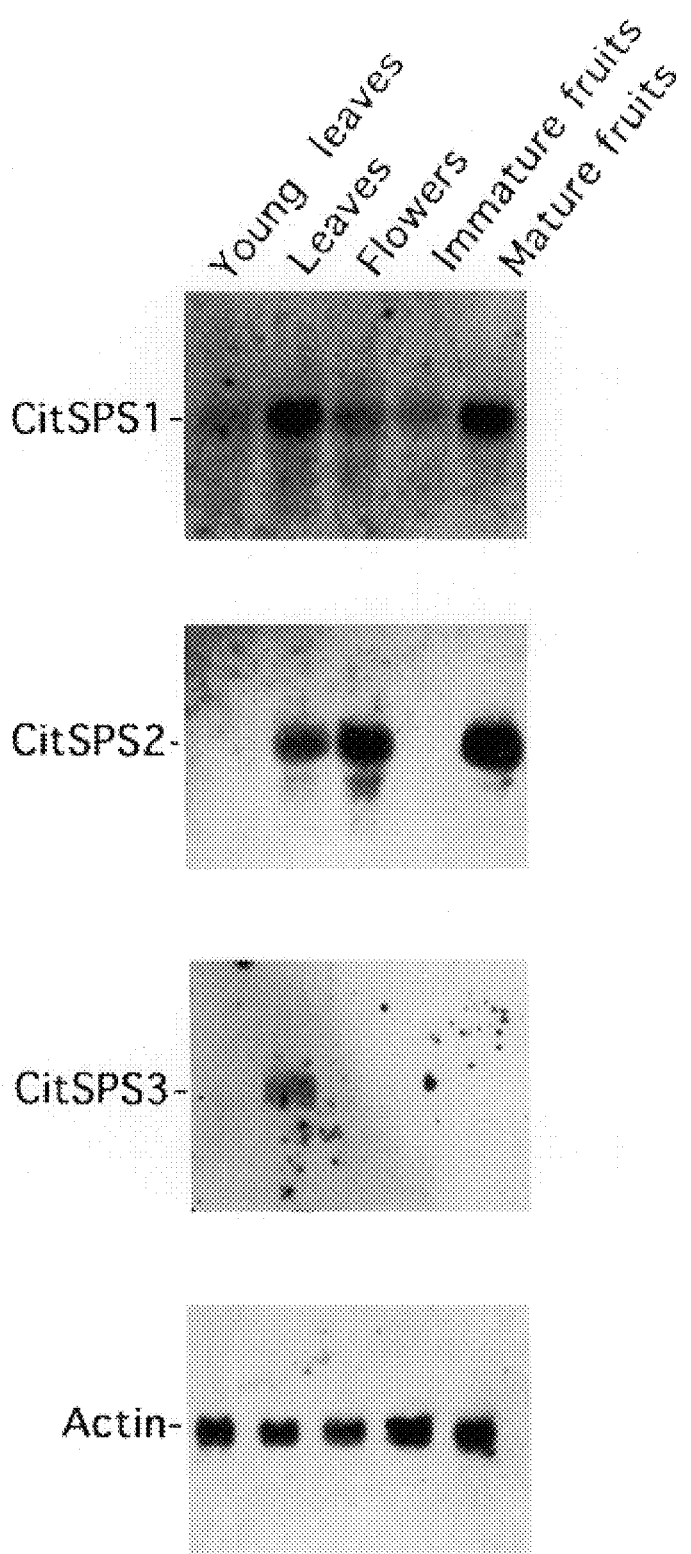
FIG. 6 shows a Northern blot analysis of total RNA from citrus using CitSPS1, pSPS2 and pSPS3 as probes and an actin probe as the loading control. Ten-microgram samples of total RNA from young leaves, leaves, flowers, immature fruits and mature fruits were fractionated by electrophoresis on 1.0% agarose gel including 2.2 M formamide and transferred to Hybond-N membrane.

As seen in FIG. 6, hybridization signals compatible with the length of CitSPS1 were obtained, with an estimated transcription size of 3.5 kb. CitSPS1 transcripts were detected in all organs at varying levels; and the amount of CitSPS1 transcripts was higher in mature leaves and fruits, but lower in immature leaves, flowers and immature fruits. Northern blot analysis using pSPS2 as a probe gave results similar to those with CitSPS1, but the levels of CitSPS2 transcripts were scarcely detectable in immature leaves and fruits, while being low in mature leaves and high in flowers and mature fruits. These results suggest that the expression of CitSPS1 or CitSPS2 is not organ-specific because both are found in source and sink organs, but is stage-specifically regulated. On the other hand, the approximately 3.5 kb CitSPS2 transcript was merely detected in young leaves and mature leaves. Furthermore, there was not detected any significant transcript in young leaves and flowers by pSPS3, while a weak signal was detected in mature leaves.

These results reveal that the three SPS isoforms were differently expressed specifically in the organ and developmental stage.

Example 5

Extraction and Assay of SPS

SPS was extracted from C. unshiu albedo/flavedo peel or juice sacs/segment epidermis of fruits harvested 89, 120, 148, 187 and 223 days after flowering that have been frozen in a liquid nitrogen. The tissue was homogenized and extracted in a chilled 100 mM MOPS-NaOH buffer (pH 7.5) containing 5 mM $MgCl_2$, 0.5 mg/ml BSA, 2.5 mM ditiothreitol (DTT), 0.05% Triton X-100, 10 mM K-ascorbate, 2% glycerol, 1 mM EDTA and 2% polyvinylpolypyrrolidone (PVPP) in a homogenizer. Tissue-to-buffer ratio was 1:3. After centrifugation at 10,000×g for 10 min, the supernatant was loaded onto a PD-10 column previously equilibrated with same buffer according to the supplier's instruction (Pharmacia). Unless otherwise prescribed, all procedures were carried out at 4° C. Protein content was measured as described in Bradford, M. M. (1976) Anal. Biochem. 72:248–254, using a BSA standard.

The reaction mixture (250 μl) to determine SPS activity was composed of 50 mM MOPS-NaOH (pH 7.5), 15 mM $MgCl_2$, 5 mM fructose 6-P, 15 mM glucose 6-P, 10 mM UDPG and 150 μl of the desalted extract. Reaction mixtures were incubated at 30° C. and terminated at 0 and 30 min with 250 μl of 30% KOH. Tubes were placed in boiling water for 10 min to destroy any unreacted fructose. After cooling, 3.5 ml of a mixture of 0.14% anthrone in 13.8 M H₂SO₄ was added and incubated in a chamber at 37° C. for 20 min. After cooling, color development was measured at 620 nm.

As a result, the formation of the product was linear in relation to the time and the amount of an extract added to the assay, and the SPS activity of about 200 μmol UDP/hr/mg protein was recovered from the juice sacs/segment epidermis of mature fruits harvested 223 days after flowering.

What is claimed is:

1. An isolated DNA encoding a sucrose phosphate synthase from Citrus which comprises the amino acid sequence of SEQ ID NO:2.

2. The DNA of claim 1, which comprises SEQ ID NO:1.

3. The DNA of claim 1, wherein the sucrose phosphate synthase consists of the amino acid sequence of SEQ ID NO:2.

4. The DNA of claim 1, which consists of SEQ ID NO:1.

* * * * *